United States Patent [19]

Ham et al.

[11] Patent Number: 5,792,885

[45] Date of Patent: Aug. 11, 1998

[54] PREPARATION OF 3-AMINO-1-HYDROXYPROPANE-1, 1-DIPHOSPHONIC ACID

[75] Inventors: Won Hun Ham; Young Hun Jung; Chang Young Oh; Kee Young Lee; Yong Hyun Kim, all of Suwon, Rep. of Korea

[73] Assignee: Dong Kook Pharmaceutical Co., Ltd., Seoul, Rep. of Korea

[21] Appl. No.: 910,851

[22] Filed: Aug. 13, 1997

[30] Foreign Application Priority Data

Sep. 3, 1996 [KR] Rep. of Korea ............ 1996-37983

[51] Int. Cl.$^6$ .................................. C07F 9/38

[52] U.S. Cl. ........................................ 562/13

[58] Field of Search .................................. 562/13

[56] References Cited

U.S. PATENT DOCUMENTS

| | | | |
|---|---|---|---|
| 4,304,734 | 12/1981 | Jary et al. | 562/13 |
| 4,719,203 | 1/1988 | Bosies et al. | 514/108 |
| 4,927,814 | 5/1990 | Gall et al. | 562/13 X |
| 5,019,651 | 5/1991 | Kieczykowski et al. | 562/13 |

FOREIGN PATENT DOCUMENTS 2 130 794  1/1973  Germany.

*Primary Examiner*—Michael G. Ambrose
*Attorney, Agent, or Firm*—Meltzer, Lippe, Goldstein et al.

[57] ABSTRACT

A preparation of 3-amino-1-hydroxypropane-1,1-diphosphonic acid includes the steps of: mixing N-alkoxycarbonyl-β-alanine, phosphorous chloride and phosphorous acid in the ratio of 1:1:1~1:3:3 in a reaction solvent, xylene at 70°–140° C.; hydrolyzing; and obtaining 3-amino-1-hydroxypropane-1,1-diphosphonic acid as a product, thus decreasing the production of unidentified by-products and giving and low production cost by using xylene instead of chlorobenzene as a reaction solvent.

5 Claims, No Drawings

PREPARATION OF 3-AMINO-1-HYDROXYPROPANE-1, 1-DIPHOSPHONIC ACID

BACKGROUND OF THE INVENTION

1. Field of the Invention

The present invention relates to an improved preparation of 3-amino-1-hydroxypropane-1,1-diphosphonic acid of the formula given by

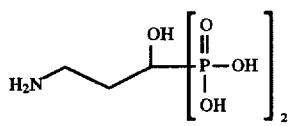

2. Discussion of Related Art 3-amino-1-hydroxypropane-1,1-diphosphonic acid is a useful compound as a remedy for osteoporosis. Osteoporosis is a disease of decreasing the density of bones to an abnormal level, prevalent for old persons, especially women in menopause. Symptoms of the disease may include sharp pain such as lumbago, reduction of stature and diseased bone fracture based on the relative seriousness of the decrease in the mineral contents of bones.

With the effort put into the development of cure for osteoporosis, many studies have been made on the efficient preparation of 3-amino-1-hydroxypropane-1,1-diphosphonic acid that is known as a conventional effective cure, for example, a method disclosed in DE Patent No. 2,130,794, mixing β-alanine, phosphorous trichloride and phosphorous acid in chlorobenzene. However, the yield and purity of the final product are very low and an unidentified yellowish red amorphous phosphorous-oxygen compound is obtained as a by-product. Thus required separation of the by-product is not only difficult, but also leads to high production cost.

According to another method, 3-amino-1-hydroxypropane-1,1-diphosphonic acid is prepared by mixing β-alanine with phosphorous oxychloride and phosphorous acid in chlorobenzene, followed by a hydrolysis. The method also results in unsatisfactory yield and purity of the final product.

SUMMARY OF THE INVENTION

Accordingly, the present invention is directed to a preparation of 3-amino-1-hydroxypropane-1,1-diphosphonic acid that substantially obviates one or more of the problems due to limitations and disadvantages of the related art.

An object of the present invention is to provide an improved preparation of 3-amino-1-hydroxypropane-1,1-diphosphonic acid using N-alkoxycarbonyl-β-alanine as a start material in xylene as a reaction solvent to increase the yield of final products with a high purity.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof.

To achieve these and other advantages and in accordance with the purpose of the present invention, as embodied and broadly described, a preparation of 3-amino-1-hydroxypropane-1,1-diphosphonic acid comprises the steps of: mixing N-alkoxycarbonyl-β-alanine, phosphorous chloride and phosphorous acid in the ratio of 1:1:1~1:3:3 in a reaction solvent, xylene at 70°–140° C.; hydrolyzing; and obtaining 3-amino-1-hydroxypropane-1,1-diphosphonic acid as a product.

It is to be understood that both the foregoing general description and the following detailed description are exemplary and explanatory and are intended to provide further explanation of the invention as claimed.

DETAILED DESCRIPTION OF PREFERRED EMBODIMENT

Reference will now be made in detail to the preferred embodiments of the present invention.

The start material is N-alkoxycarbonyl-β-alanine obtained by the reaction of β-alanine and choloroformate. 1–3 moles of N-alkoxycarbonyl-β-alanine, 1–3 moles of phosphorous pentachloride or phosphorous trichloride, and 1–3 moles of phosphorous acid are mixed in the ratio of 1:1:3~1:3:3, preferably 1:1:1, at 70°–140° C.

The chloroformate is methyl chloroformate, ethyl chloroformate, isopropyl chloroformate, propyl chloroformate, allyl chloroformate, t-butyl chloroformate, or benzyl chloroformate.

The reaction mixture undergoes hydrolysis by using water at 25°–110° C. After a separation of aqueous phase, 3-amino-1-hydroxypropane-1,1-diphosphonic acid was obtained.

Methanol may be added to increase the yield of 3-amino-1-hydroxypropane-1,1-diphosphonic acid. The amount of methanol added is about 150–250 ml, preferably 200 ml. The ratio of xylene to methanol is 2.0–3.2:1, preferably 2.5:1.

EXAMPLE OF PREPARATION (N-ALKOXYCARBONYL-β-ALANINE)

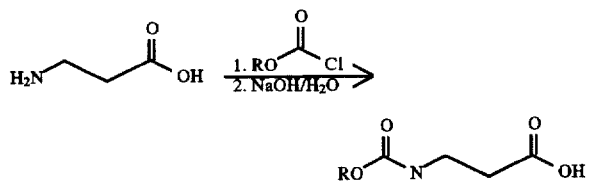

wherein, R is $CH_3$, $CH_3CH_2$, $(CH_3)_2CH$, $CH_3CH_2CH_2$, $CH_2=CHCH_2$, $(CH_3)_3C$ OR $PhCH_2$ 1N NaOH was dropped into the mixed solution of 17.8 g (0.2 moles) of β-alanine and 1N NaOH (200 ml) to keep pH between 9.0 and 9.5. 105 moles of chloroformic acid was added by 2~3 moles for 1 hour. The temperature of the resulting mixture was lowered to 0 degrees Celsius. Then the desired mixture extracted with ether(3×100 ml), and pH was adjusted to 1 with phosphoric acid. Aqueous phase was saturated with sodium chloride and extracted three times with 100 ml of M.C. (Methylene Chloride). After the vaporization of organic phase, 85% yield of N-alkoxycarbonyl-β-alanine was obtained.

PREFERRED EMBODIMENT 1

123.00 g (1.5 mol) of phosphorous acid was added to the suspension of phosphorous pentachloride (312.36 g, 1.5 mol) in xylene (500 ml) to give an exothermic reaction. The resultant transparent solution was cooled to a room temperature and 147.13 g (1.5 mol) of prepared N-alkoxycarbonyl-β-alanine was added to the cooled solution. After stirred for 15 minutes and slowly heated to 100° C. the mixture was refluxed for 5 hours. The mixture was then cooled to room temperature and 1000 ml of water was added to it. The mixture was slowly heated to 100° C. again to undergo a reflux for 5 hours. Aqueous phase is then separated and cooled to give a final product in 65% yield.

To identify the final product, the measurement of infrared spectrum was done by using KBr pellets with Model 621 infrared spectrophotometer manufactured by Perking-Elmer. After another measurement of NMR spectrum using $D_2O$ that used EM-390-90 MHz spectrophotometer, the final product was identified as 3-amino-1-hydroxypropane-1,1-diphosphonic acid. The results of the analyses were as follows:

IR: wide peak in 2900–3200 $cm^{-1}$, peak in 1600-540 $cm^{-1}$ NMR: multiplet at 2.2 ppm, triplet at 3.3 ppm From the radioactivation purity analysis for the product was performed by using β-alanine (1-$^{14}$C) from ICN Chemical & Radioisotope Division as a radioactive labelled start material, the specific activity of the β-alanine (1-$^{14}$C) was 13.9 mCi/mmole. To measure the purity of the final product, a Model 7220/21 scanner manufactured by Packard was used for a radioactive scanning, an LS 9000 liquid scintillation counter for the measurement of specific activity, and polygram cell 300 cellulose plate for TLC (Thin-Layer Chromatography). As a result, the final product was turned out to be a pure single substance since a single peak was observed from the product.

radioactivation purity: water:ethanol:aluminum hydroxide=80:10:15, r.f. 0.8 water:acetone=70:30, r.f.0.2 formic acid:water=1:1, r.f. 1.0

EMBODIMENT 2

147.13 g (1 mol) of N-alkoxycarbonyl-β-alanine was added to 500 ml of xylene, followed by the addition of 137.33 g (1 mol) of phosphorous trichloride and 32.00 g (1 mol) of phosphorous acid. The mixture was slowly heated to 100° C. and refluxed for 5 hours. Cooled to a room temperature, 1000 ml of water was added to the mixture and then the mixture was heated again to 100° C. and refluxed for 5 hours. Aqueous phase is then separated out from the mixture and the remainder was concentrated under reduced pressure to give a final product in 63% yield.

From IR and NMR measurements, the final product was identified as 3-amino-1-hydroxypropane-1,1-diphosphonic acid.

EMBODIMENT 3

Excepting that 200 ml of methanol was added to the aqueous phase separated after the hydrolysis in order to promote the crystallization, the same procedures as the embodiment 1 were repeated to give a final product. From IR and NMR measurements, the final product was identified as 3-amino-1-hydroxypropane-1,1-diphosphonic acid and the yield was 72.0%.

EMBODIMENT 4

Excepting that 200 ml of methanol was added to the aqueous phase separated after the hydrolysis in order to promote the crystallization, the same procedures as the embodiment 2 were repeated to give a final product. From IR and NMR measurements, the final product was identified as 3-amino-1-hydroxypropane-1,1-diphosphonic acid and the yield was 69.1%.

COMPARATIVE EXAMPLES

Excepting that chlorobenzene was used as a reaction solvent instead of 500 ml of xylene, the same procedures as the embodiment 1 and 2 were repeated to produce 3-amino-1-hydroxypropane-1,1-diphosphonic acid and their yields were 35% and 32% respectively.

From the results of the embodiments and comparative examples, the yield of product becomes smaller than before when xylene is substituted with chlorobenzene as a reaction solvent. It is supposed that by-products of the reaction have relatively large specific gravity and they are greater than the final product in the production yields and the specific gravity of the organic phase containing the products becomes equivalent to that of the aqueous phase. As a result, the use of chlorobenzene decreases the efficiency of separation of the organic phase containing the final product.

As shown in embodiments 3 and 5, the yield of 3-amino-1-hydroxypropane-1,1-diphosphonic acid was increased when methanol was added.

According to the present invention, the amount of unidentified by-products is reduced and an efficient phase separation takes place between the by-products dissolved in xylene layer and the final product in aqueous layer. Thus, the final product, highly pure 3-amino-1-hydroxypropane-1,1-diphosphonic acid can be obtained with high yield. It may be expected to reduce the production cost by using xylene as a reaction solvent since it is less expensive than chlorobenzene.

It will be apparent to those skilled in the art that various modifications and variations can be made in the preparation of 3-amino-1-hydroxypropane-1,1-diphosphonic acid of the present invention without departing from the spirit or scope of the invention. Thus, it is intended that the present invention cover the modifications and variations of this invention provided they come within the scope of the appended claims and their equivalents.

What is claimed is:

1. A preparation of 3-amino-1-hydroxypropane-1,1-diphosphonic acid, comprising the steps of:

mixing N-alkoxycarbonyl-β-alanine, phosphorous chloride and phosphorous acid in the mole ratio of 1:1:1~1:3:3 in xylene as a reaction solvent at 70°~140° C.;

hydrolyzing; and carrying out a phase separation to obtain 3-amino-1-hydroxypropane-1,1-diphosphonic acid as a product.

2. The preparation as defined in claim 1, wherein 150–250 ml of methanol is added in the ratio of xylene to methanol 2.0~3.2:1.

3. The preparation as defined in claim 1, wherein the N-alkoxycarbonyl-β-alanine, phosphorous chloride and phosphorous acid are mixed in the mole ratio of 1:1:1.

4. The preparation as defined in claim 1, wherein the phosphorous chloride is phosphorous pentachloride or phosphorous trichloride.

5. The preparation as defined in claim 3, wherein the phosphorous chloride is phosphorous pentachloride or phosphorous trichloride.

* * * * *